(12) United States Patent
Schott et al.

(10) Patent No.: US 8,339,769 B2
(45) Date of Patent: Dec. 25, 2012

(54) METHOD OF PRODUCING A CAPACITOR

(75) Inventors: Joachim Hossick Schott, Minneapolis, MN (US); Brian Melody, Greer, SC (US); John Tony Kinard, Greer, SC (US)

(73) Assignees: Medtronic, Inc., Minneapolis, MN (US); Kemet Electronics Corporation, Greenville, SC (US)

( * ) Notice: Subject to any disclaimer, the term of this patent is extended or adjusted under 35 U.S.C. 154(b) by 1197 days.

(21) Appl. No.: 12/129,499

(22) Filed: May 29, 2008

(65) Prior Publication Data
US 2008/0229565 A1   Sep. 25, 2008

Related U.S. Application Data

(60) Division of application No. 11/440,922, filed on May 25, 2006, now Pat. No. 7,499,260, which is a continuation of application No. 11/003,183, filed on Dec. 3, 2004, now Pat. No. 7,079,377, which is a continuation-in-part of application No. 10/260,682, filed on Sep. 30, 2002, now Pat. No. 7,002,790, and a continuation-in-part of application No. 10/448,556, filed on May 30, 2003, now abandoned.

(51) Int. Cl.
*H01G 9/04* (2006.01)

(52) U.S. Cl. ........ 361/516; 438/171; 438/190; 438/210; 361/503; 361/508; 361/521

(58) Field of Classification Search .............. 438/171, 438/190, 210, 238, 250, 379–381
See application file for complete search history.

(56) References Cited

U.S. PATENT DOCUMENTS

| | | | |
|---|---|---|---|
| 3,243,316 A | 3/1966 | O'Nan et al. | |
| 3,612,956 A | 10/1971 | Sterling et al. | |
| 3,618,615 A | 11/1971 | Greatbatch | |
| 4,090,231 A | 5/1978 | Millard et al. | |
| 4,523,255 A | 6/1985 | Rogers | |
| 4,562,511 A | 12/1985 | Nishino et al. | |
| 4,780,794 A | 10/1988 | Mase et al. | |
| 4,780,797 A | 10/1988 | Libby | |
| 4,910,645 A | 3/1990 | Jonas et al. | |
| 4,942,500 A | 7/1990 | Libby et al. | |

(Continued)

FOREIGN PATENT DOCUMENTS

DE   30 11 701   10/1981

(Continued)

OTHER PUBLICATIONS

Conway, "The Double Layer and Surface Functionalities at Carbon," Electrochemical Supercapacitors: Scientific Fundamentals and Technological Applications, Chapter 9 (1999) (58 sheets).

(Continued)

*Primary Examiner* — Mamadou Diallo
(74) *Attorney, Agent, or Firm* — Foley & Lardner LLP

(57) ABSTRACT

A method of making an electrolytic capacitor includes providing a first electrode that includes a metal substrate, a carbide layer, and a carbonaceous material. The metal substrate includes a metal selected from the group consisting of titanium, aluminum, tantalum, niobium, zirconium, silver, steel, and alloys and combinations thereof. The method further includes providing a second electrode and an electrolyte.

34 Claims, 7 Drawing Sheets

U.S. PATENT DOCUMENTS

| | | |
|---|---|---|
| 5,043,849 A | 8/1991 | Libby |
| 5,098,485 A | 3/1992 | Evans |
| 5,187,788 A | 2/1993 | Marmelstein |
| 5,312,439 A | 5/1994 | Loeb |
| 5,331,579 A | 7/1994 | Maguire, Jr. et al. |
| 5,369,547 A | 11/1994 | Evans |
| 5,469,325 A | 11/1995 | Evans |
| 5,507,966 A | 4/1996 | Liu |
| 5,531,772 A | 7/1996 | Prutchi |
| 5,541,863 A | 7/1996 | Magor et al. |
| 5,559,667 A | 9/1996 | Evans |
| 5,622,746 A | 4/1997 | Hahn et al. |
| 5,671,415 A | 9/1997 | Hossain |
| 5,729,427 A | 3/1998 | Li et al. |
| 5,737,181 A | 4/1998 | Evans |
| 5,754,394 A | 5/1998 | Evans et al. |
| 5,786,980 A | 7/1998 | Evans |
| 5,800,706 A | 9/1998 | Fischer |
| 5,822,177 A | 10/1998 | Popp et al. |
| 5,849,031 A | 12/1998 | Martinez et al. |
| 5,851,506 A | 12/1998 | Zheng et al. |
| 5,853,888 A | 12/1998 | Dutta et al. |
| 5,894,403 A | 4/1999 | Shah et al. |
| 5,926,362 A | 7/1999 | Muffoletto et al. |
| 5,932,185 A | 8/1999 | Pekala et al. |
| 5,980,977 A | 11/1999 | Deng et al. |
| 5,982,609 A | 11/1999 | Evans |
| 5,985,112 A | 11/1999 | Fischer |
| 6,031,711 A | 2/2000 | Tennent et al. |
| 6,094,339 A | 7/2000 | Evans |
| 6,099,960 A | 8/2000 | Tennent et al. |
| 6,099,965 A | 8/2000 | Tennent et al. |
| 6,128,180 A | 10/2000 | Araki et al. |
| 6,154,358 A | 11/2000 | Fukaumi et al. |
| 6,191,931 B1 | 2/2001 | Paspa et al. |
| 6,203,814 B1 | 3/2001 | Fisher et al. |
| 6,205,016 B1 | 3/2001 | Niu |
| 6,206,937 B1 | 3/2001 | Kudoh et al. |
| 6,208,502 B1 | 3/2001 | Hudis et al. |
| 6,210,450 B1 | 4/2001 | Fukaumi et al. |
| 6,221,330 B1 | 4/2001 | Moy et al. |
| 6,288,890 B1 | 9/2001 | Saito et al. |
| 6,352,564 B1 | 3/2002 | Araki et al. |
| 6,356,433 B1 | 3/2002 | Shi et al. |
| 6,381,121 B1 | 4/2002 | Monden et al. |
| 6,414,836 B1 | 7/2002 | Tennent et al. |
| 6,419,717 B2 | 7/2002 | Moy et al. |
| 6,426,863 B1 | 7/2002 | Munshi |
| 6,432,866 B1 | 8/2002 | Tennent et al. |
| 6,442,016 B2 | 8/2002 | Fukuyama et al. |
| 6,459,565 B1 | 10/2002 | Lessner et al. |
| 6,491,789 B2 | 12/2002 | Niu |
| 6,514,897 B1 | 2/2003 | Moy et al. |
| 6,515,847 B1 | 2/2003 | Naraya |
| 6,519,137 B1 | 2/2003 | Nitta et al. |
| 6,674,635 B1 | 1/2004 | Fife et al. |
| 6,687,118 B1 | 2/2004 | O'Phelan et al. |
| 6,818,517 B1 | 11/2004 | Maels |
| 6,842,328 B2 | 1/2005 | Schott et al. |
| 6,855,594 B1 | 2/2005 | Bhat et al. |
| 7,079,377 B2 | 7/2006 | Schott et al. |
| 7,256,982 B2 | 8/2007 | Lessner et al. |
| 2002/0044405 A1* | 4/2002 | Muffoletto et al. ........... 361/502 |
| 2002/0075634 A1 | 6/2002 | Uenishi et al. |
| 2002/0095860 A1 | 7/2002 | Moy et al. |
| 2002/0146895 A1 | 10/2002 | Ramdani et al. |
| 2002/0171996 A1 | 11/2002 | Yu et al. |
| 2003/0010407 A1 | 1/2003 | Arai |
| 2003/0035769 A1 | 2/2003 | Moy et al. |
| 2003/0044519 A1 | 3/2003 | Takai |
| 2003/0103319 A1 | 6/2003 | Kumar et al. |
| 2003/0172509 A1 | 9/2003 | Maletin et al. |
| 2004/0064155 A1 | 4/2004 | Norton et al. |
| 2004/0085711 A1 | 5/2004 | Merker et al. |
| 2004/0106041 A1 | 6/2004 | Reynolds et al. |

FOREIGN PATENT DOCUMENTS

| | | |
|---|---|---|
| DE | 198 36 651 | 2/2000 |
| EP | 1 207 567 A2 | 5/2002 |
| JP | 63314766 A | 12/1988 |
| JP | 3-4512 A | 1/1991 |
| JP | 08162374 A | 6/1996 |
| JP | 2001-110685 A | 4/2001 |
| WO | WO 97/43774 | 11/1997 |
| WO | WO 00/02213 | 1/2000 |
| WO | WO 02/43090 A2 | 5/2002 |
| WO | WO 2004/032163 A1 | 4/2004 |

OTHER PUBLICATIONS

Dresselhaus et al., "Carbon nanotubes," Physics World, pp. 33-38, (Jan. 1998).

Hahn et al., "A 24 V Bipolar Electrochemical Double Layer Capacitor Based on Activated Glassy Carbon," In "Power Sources for the New Millenium," The Electrochemical Society, Inc. Proceedings vol. 2000-22, (9 pages) (2001).

Li et al., "Highly-ordered carbon nanotube arrays for electronics applications," Applied Physics Letters 73 (3), pp. 367-369, (1999).

Loeb et al., "Injectable microstimulator for functional electrical stimulation," Med.& Biol. Eng. & Comput., 29, NS13-NS19 (1991), 7 pages.

Niu et al., "High power electrochemical capacitors based on carbon nanotube electrodes," Applied Physics Letters 70, Mar. 17, 1997, 6 pages.

Raistrick, "Electrochemical Capacitors," Electrochemistry of Semiconductors and Electronics, Chapter 7, (1992) pp. 297-355, (30 sheets).

Schönenberer et al., "Multiwall carbon nanotubes," Physics World, pp. 37-41 (Jun. 2000).

Trasatti "Properties of Conductive Transition Metal Oxides with Rutile-Type Structure," Chapter 7, Electrodes of Conductive Metallic Oxides Part A., pp. 301-358 (1980) (58 sheets).

Trasatti; et al., "Ruthenium dioxide: a new interesting electrode material,"J. Electroanal. Chem., 29, App. 1-5, (1971).

Carlberg et al. "Poly(3,4-ethylenedioxythiophene) as electrode material in electrochemical capacitors," Journal of Electrochemical Society, 1997, vol. 144, pp. L61-L64.

Conway, B.E., "Electrochemical Supercapacitors" Scientific Fundamentals and Technological Applications, Chapters 9-11, cover page and pp. 183-295, Kluwer Academic / Plenum Publishers.

Non-Final Office Action for U.S. Appl. No. 11/891,084, dated Nov. 26, 2008, 18 pages.

International Search Report and Written Opinion for International Application No. PCT/US2004/016469; mailed Oct. 28, 2004; 15 pages.

\* cited by examiner

METHOD OF PRODUCING A CAPACITOR

CROSS-REFERENCE TO RELATED PATENT APPLICATIONS

This application is a Divisional of U.S. patent application Ser. No. 11/440,922 filed May 25, 2006, which is a Continuation of U.S. patent application Ser. No. 11/003,183 filed Dec. 3, 2004, which is a Continuation-in-Part of both U.S. patent application Ser. No. 10/448,556 filed May 30, 2003 and U.S. patent application Ser. No. 10/260,682 filed Sep. 30, 2002. The entire disclosures the following applications are expressly incorporated by reference herein in their entirety: U.S. patent application Ser. Nos. 11/440,922; 11/003,183; 10/448,556; and U.S. patent application Ser. No. 10/260,682.

This application is also related to U.S. patent application Ser. No. 10/449,879 and U.S. patent application Ser. No. 10/449,645, each of which were filed on May 30, 2003.

BACKGROUND

The present invention relates generally to the field of capacitors. More specifically, the present invention relates to electrolytic capacitors for use in a device such as an implantable medical device.

Since their earliest inception, there has been significant advancement in the field of body-implantable electronic medical devices. Today, such implantable devices include therapeutic and diagnostic devices, such as pacemakers, cardioverters, defibrillators, neural stimulators, drug administering devices, and the like for alleviating the adverse effects of various health ailments.

Implantable medical devices may utilize a capacitor to perform various functions. For example, if the implantable medical device is a defibrillator, one or more capacitors may be used to provide a therapeutic high voltage treatment to a patient.

One type of capacitor that may be used in such an application is an electrolytic or wet slug capacitor. Conventional wet slug capacitors may include a container formed from tantalum or a tantalum alloy that acts as the cathode. An electrolyte (e.g., an acid such as phosphoric acid) and an anode are provided within the container. In these types of capacitors, an anodic oxide may be formed on exposed surfaces.

Since the electrolyte is electrically conductive, a conductor-insulator-conductor structure including metal, oxide coating, and electrolyte is present at both the anode and the cathode. Each of these conductor-insulator-conductor structures constitute themselves a capacitor.

In the conventional wet slug capacitor, the anode capacitance is electrically connected in series with the cathode capacitance. The total capacitance $C_{total}$ of the two capacitors $C_{anode}$ and $C_{cathode}$ in series is expressed by the formula $1/C_{total}=1/C_{anode}+1/C_{cathode}$. In order to maximize $C_{total}$, the capacitance $C_{cathode}$ has to be as large as possible.

Although conventional wet slug capacitors having useful capacitances have been produced, there is a desire to increase the energy per unit volume of capacitor anode (i.e., the stored energy density). The energy E stored inside a capacitor may be expressed by the formula $E=\frac{1}{2}C_{total}U^2$, where U is the potential to which the capacitor is charged. Hence, high energy density requirements demand high-capacitance per-unit area cathodes so as to maximize $C_{total}$ and, in turn, E. Conventional capacitor cathode materials (e.g., tantalum), however, may provide a limited capacitance per unit area. For certain applications, it is desirable to provide a capacitor cathode that has a capacitance in the range of approximately 10-20 milliFarads per square centimeter of geometrical surface area.

Accordingly, there is a need to provide an electrode for a capacitor that utilizes a material which enhances the capacitance for the electrode relative to conventional capacitor electrodes (e.g., provides a capacitor electrode having a specific capacitance of greater than approximately 10 milliFarads per square centimeter). It would be desirable to provide a method of producing such an electrode using a method which is relatively simple in terms of the processing involved and that does not adversely affect capacitor performance. There is also a need for an electrode that utilizes a material which produces a relatively smooth and defect-free electrode surface. There is further a need to provide a capacitor that includes at least one electrode that exhibits increased capacitance as compared to conventional capacitor electrodes.

It would be desirable to provide an electrode for a capacitor and a capacitor that provides one or more of these or other advantageous features. Other features and advantages will be made apparent from the present description. The teachings disclosed extend to those embodiments that fall within the scope of the appended claims, regardless of whether they provide one or more of the aforementioned advantages.

SUMMARY

An exemplary embodiment of the invention relates to a method of making an electrolytic capacitor that includes providing a first electrode that includes a metal substrate, a carbide layer, and a carbonaceous material. The metal substrate includes a metal selected from the group consisting of titanium, aluminum, tantalum, niobium, zirconium, silver, steel, and alloys and combinations thereof. The method further includes providing a second electrode and an electrolyte.

Another exemplary embodiment of the invention relates to a method of making an electrolytic capacitor that includes preparing a first electrode by providing a carbide layer and a carbonaceous layer on a metal substrate. The carbonaceous layer includes activated carbon and the metal substrate includes a metal selected from the group consisting of titanium, aluminum, tantalum, niobium, zirconium, silver, and steel, and alloys and combinations thereon. The method also includes providing the first electrode in a housing along with a second electrode and an electrolyte.

Another exemplary embodiment of the invention relates to a method of making an electrolytic capacitor that includes providing a first layer of material and a second layer of material on a substrate to form a first electrode. The first layer of material includes a carbide and the second layer of material includes a carbonaceous material. The substrate is formed from a metal selected from the group consisting of titanium, aluminum, tantalum, niobium, zirconium, silver, and steel, and alloys and combinations thereof. The method also includes providing the first electrode, a second electrode, and an electrolyte in a housing.

BRIEF DESCRIPTION OF THE DRAWINGS

The invention will be explained in more detail in the following text with reference to the attached drawings, in which.

DETAILED DESCRIPTION

With reference to the accompanying FIGURES, the present disclosure relates to capacitors (e.g., electrolytic capacitors) for use in medical devices (e.g., implantable medical devices), methods of producing such capacitors, and medical devices which utilize such capacitors. While the subject matter herein is presented in the context of the use of such capacitors in the field of implantable medical devices, such capacitors may be utilized in alternative applications such as external medical devices or other devices utilizing a capacitor, as will be appreciated by those of skill in the art who review this disclosure.

Figure 1:
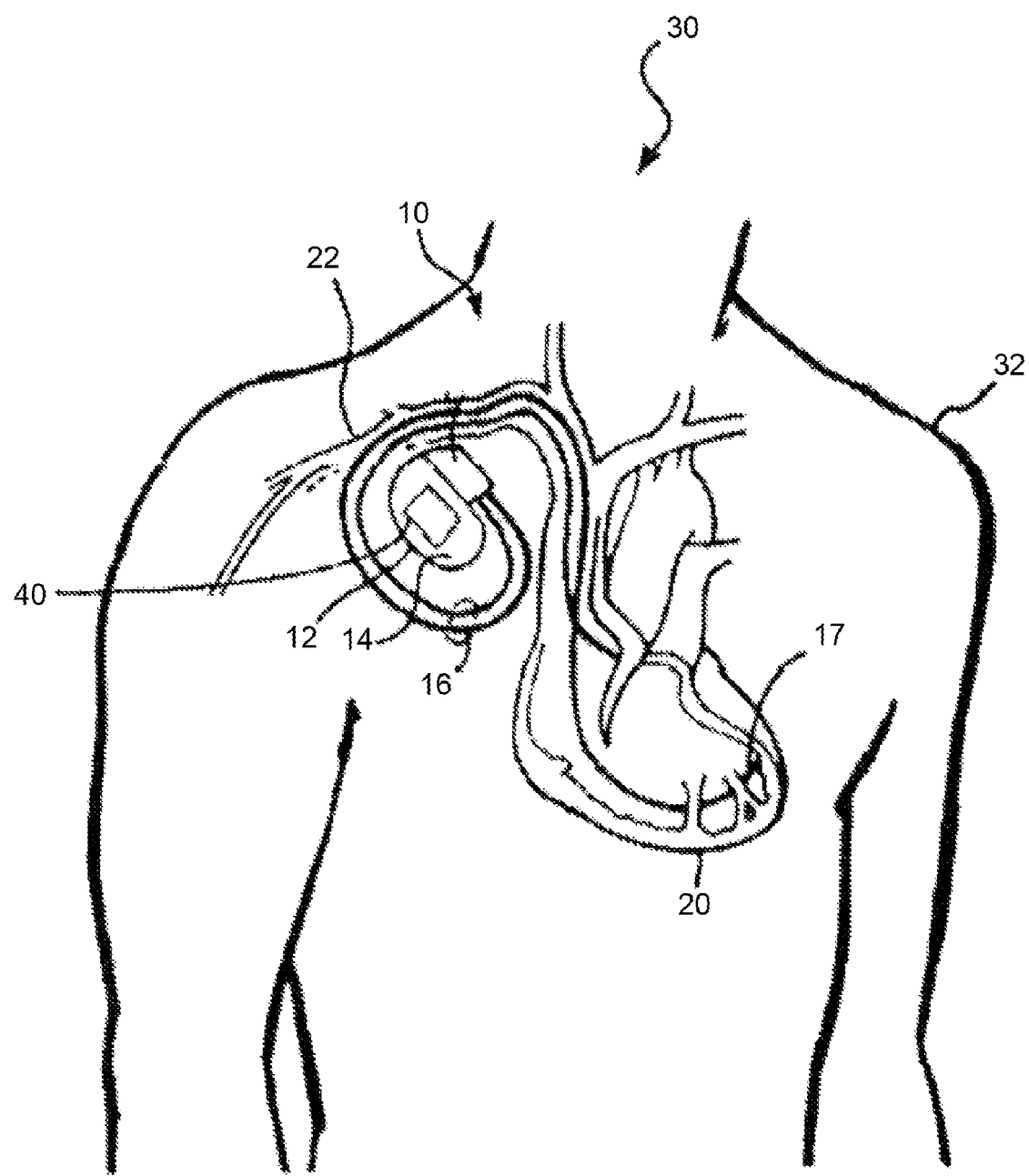
FIG. 1 is a schematic drawing showing an implantable medical device shown in the form of a defibrillator implanted within a human body.

Referring to FIG. 1, a system 10 including an implantable medical device (IMD) is shown as being implanted within a body or torso 32 of a patient 30. The system 10 includes a device 12 in the form of an implantable medical device that for purposes of illustration is shown as a defibrillator. The defibrillator is configured to provide a therapeutic high voltage (e.g., 700 volt) treatment for the patient 30. While the implantable medical device is shown and described as a defibrillator, it should be appreciated that other types of implantable medical devices may be utilized according to alternative embodiments. According to still other alternative embodiments, non-implantable (e.g., externally-connected) medical devices or other types of devices may utilize capacitors as are shown and described in this disclosure.

The device 12 includes a container or housing 14 that is hermetically sealed and biologically inert according to an exemplary embodiment. The container may be made of a conductive material. One or more leads 16 electrically connect the device 12 and the patient's heart 20 via a vein 22. Electrodes 17 are provided to sense cardiac activity and/or provide an electrical potential to the heart 20. At least a portion of the leads 16 (e.g., an end portion of the leads shown as exposed electrodes 17) may be provided adjacent or in contact with one or more of a ventricle and an atrium of the heart 20.

Figure 2:
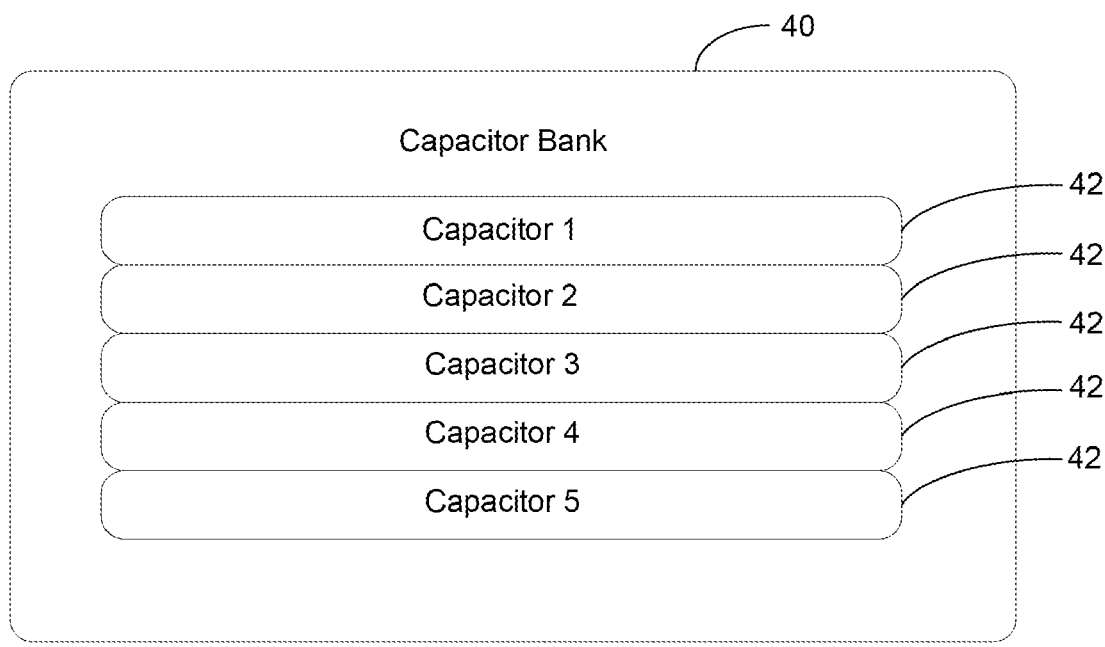
FIG. 2 is a schematic drawing of a capacitor bank for use with the implantable medical device shown in FIG. 1.

A capacitor bank 40 including a plurality of capacitors is provided within the device 12. A schematic view of the capacitor bank 40 is shown in FIG. 2, and shows a group of five capacitors 42 connected in series and provided within the capacitor bank. The size and capacity of the capacitors may be chosen based on a number of factors, including the amount of charge required for a given patient's physical or medical characteristics. According to other exemplary embodiments, the capacitor bank may include a different number of capacitors (e.g., less than or greater than five capacitors). According to still other exemplary embodiments, a different number of capacitor banks may be provided within the implantable medical device having any suitable number of capacitors provided therein.

Figure 3:
FIG. 3 is a schematic drawing showing the capacitor bank shown in FIG. 2 coupled to a battery.

As shown in FIG. 3, the capacitor bank 40 is coupled to a battery 50. According to an exemplary embodiment, the battery 50 is included within the device 12. According to alternative embodiments, the battery may be provided external to the device 12. The capacitors 42 provided within the capacitor bank are configured to store energy provided by the battery 40. For example, the system 10 may be configured such that when the device 12 determines that a therapeutic high-voltage treatment is required to establish a normal sinus rhythm for the heart 20, the capacitors 42 in the capacitor bank 40 are charged to a predetermined charge level by the battery 50. Charge stored in the capacitors 42 may then be discharged via the leads 16 to the heart 20. According to another exemplary embodiment, the capacitors may be charged prior to determination that a stimulating charge is required by the heart such that the capacitors may be discharged as needed.

Figure 4:
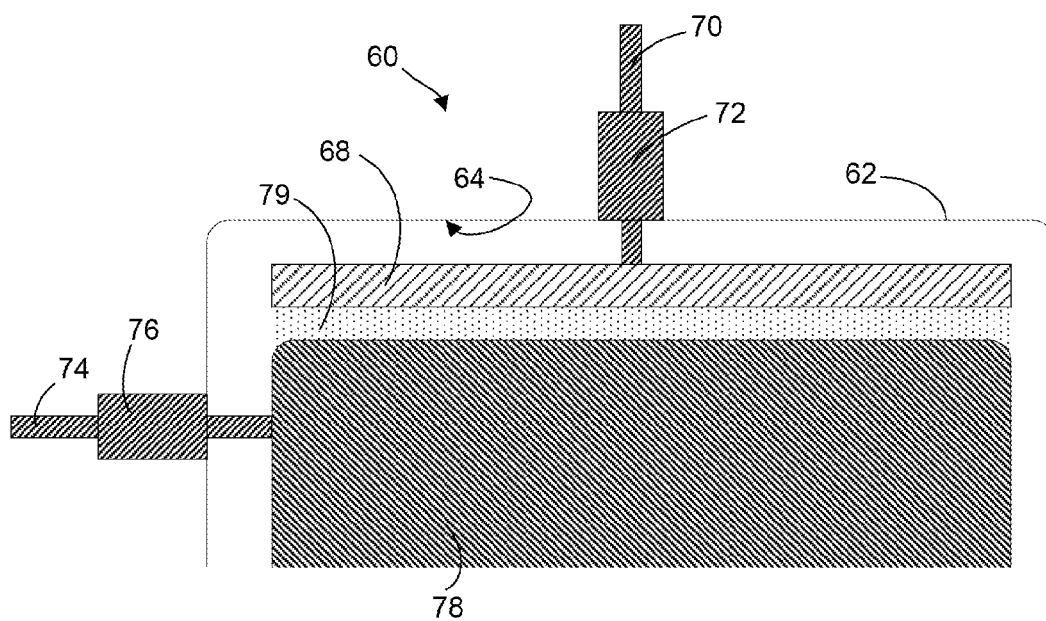
FIG. 4 is a schematic cross-sectional view of one of the capacitors provided within the capacitor bank shown in FIG. 2 according to an exemplary embodiment.

Various types of capacitors may be provided within the capacitor bank 40 according to various exemplary embodiments. FIG. 4 shows a schematic cross-sectional view of a portion of a capacitor 60 according to a first exemplary embodiment. The capacitor 60 includes a container or housing 62 (e.g., a hermetically sealed container). According to an exemplary embodiment, the container comprises titanium. According to other exemplary embodiments, other materials may be used in place of or in addition to titanium (e.g., tantalum, niobium, zirconium, etc.).

A cathode 68 is provided within the container 62. According to an exemplary embodiment, the cathode 68 is electrically isolated from an inner surface 64 of the container 62. A cathode lead 70 is electrically coupled to the cathode 68 and extends through a wall 66 of the container 62. The cathode lead 70 is electrically isolated from the container 62 by a feed-through 72. According to an exemplary embodiment, the feed-through 72 comprises an insulating material (e.g., glass) that seals the cathode lead 70 from the container 62. The feed-through 72 may also act to prevent material (e.g., electrolyte) from escaping the container 62 and to prevent foreign matter from entering the container 62 in the location of the cathode lead 70.

An anode 78 is provided within the container 62. According to an exemplary embodiment, the anode 78 comprises tantalum. According to other exemplary embodiments, the anode 78 may comprise other materials in addition to or in place of tantalum (e.g., titanium, niobium, zirconium, etc.). The anode 78 is provided in the container 62 such that it is not in direct contact with (e.g., is spaced apart from) the cathode 68.

The anode 78 is electrically coupled to an anode lead 74 that passes through a wall 66 of the container 62 via a feed-through 76. The feed-through 76 may be constructed in a similar manner as described with respect to feed-through 72, and may act to electrically isolate the anode lead 74 from the container 62 in substantially the same manner as described with respect to cathode lead 70 and feed-through 72.

An electrolyte 79 (e.g., a fluid or liquid electrolyte) is provided in the container 62. At least a portion of the electrolyte 79 is provided intermediate the cathode 68 and the anode 78. The electrolyte 79 provides negative and positive ions to constitute capacitors at the cathode 68 and the anode 78. According to an exemplary embodiment, the electrolyte 79 comprises ammonium salts (e.g., ammonium acetate) dissolved in a water and glycol mixture, phosphoric acid, etc. The particular electrolyte chosen may depend on a number of factors, such as the desired conductivity of the electrolyte.

Figure 5:
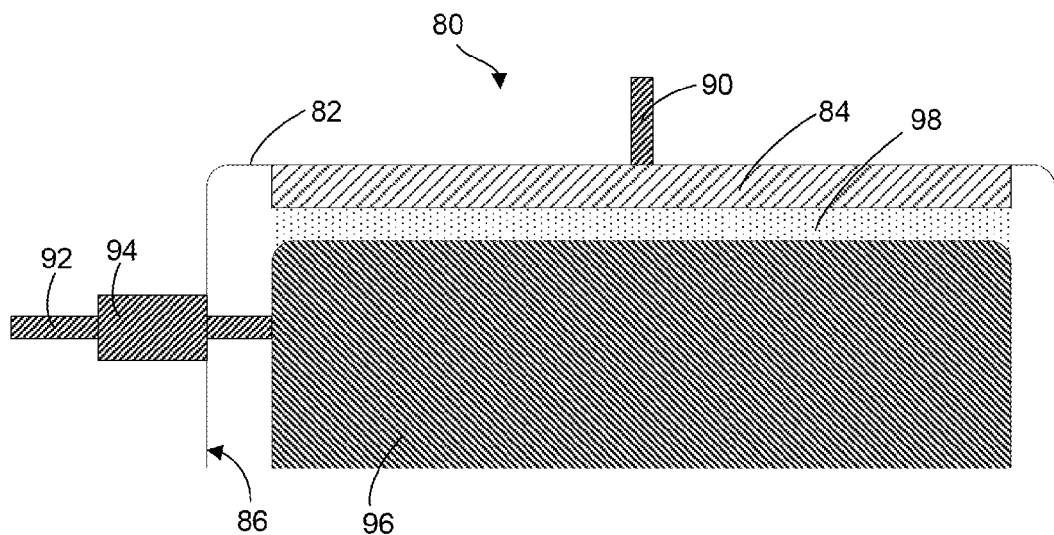
FIG. 5 is a schematic cross-sectional view of one of the capacitors provided within the capacitor bank shown in FIG. 2 according to another exemplary embodiment.

FIG. 5 shows a cross-sectional schematic view of a portion of a capacitor 80 according to another exemplary embodiment. The capacitor 80 includes a container or housing 82 which may be constructed in a manner similar to that described with respect to container 62.

A cathode 84 is integrally formed with the container 82 such that the cathode 84 forms an inner surface 86 of the container 82. The cathode 84 is electrically coupled to a cathode lead 90 that extends from the wall 88 of the container 82.

An anode 96 is provided within the container 62 such that the anode 96 is not in contact with (e.g., is spaced apart from) the cathode 84. According to an exemplary embodiment, the anode 78 comprises tantalum. According to other exemplary embodiments, the anode 78 may comprise other materials in addition to or in place of tantalum (e.g., aluminum, titanium, niobium, zirconium, etc.).

The anode 96 is electrically coupled to an anode lead 92 through a feed-through 94. The feed-through 94 may be constructed in a similar manner to that described with respect to the feed-through 72 and the feed-through 76.

An electrolyte 98 (e.g., a fluid or liquid electrolyte) is provided in the container 82. At least a portion of the electrolyte 98 is provided intermediate the cathode 84 and the anode 96 and provides negative and positive ions to constitute capacitors at the cathode 84 and the anode 96. The electrolyte utilized in the capacitor 80 may be the same as or may differ from that utilized in the capacitor 60. The particular electrolyte chosen may depend on a number of factors, such as the desired conductivity of the electrolyte.

Figure 6:
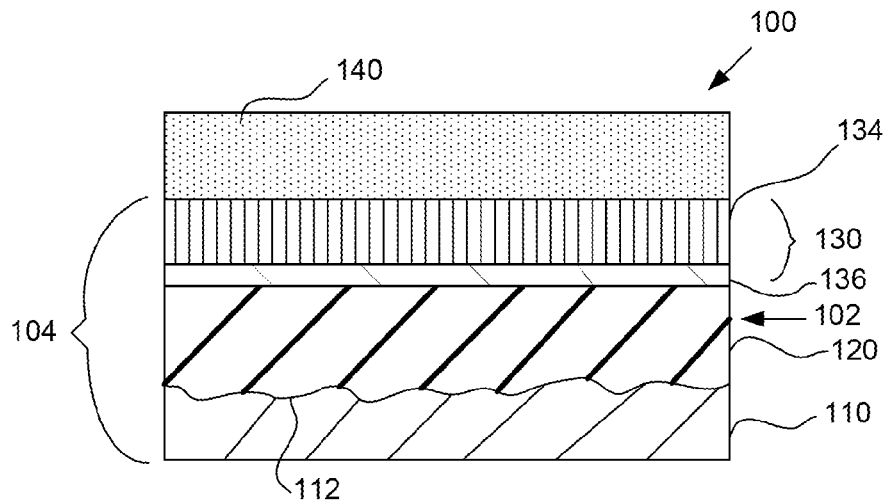
FIG. 6 is a schematic cross-sectional view of a portion of a capacitor according to an exemplary embodiment.
Figure 7:
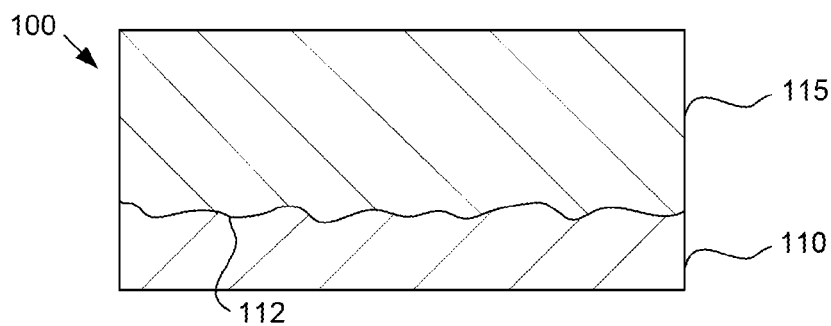
FIG. 7 is a schematic cross-sectional view of the portion of the capacitor shown in FIG. 6 showing a layer of carbon provided over a substrate.

FIG. 6 shows a more detailed schematic cross-sectional view of a portion 102 of an electrode 100 (e.g., a cathode or an anode) that may be utilized in a capacitor such as that shown in FIGS. 4 and 5. It should be noted that while two specific capacitor arrangements have been shown and described with respect to FIGS. 4 and 5, the electrode 100 may also be used with other types of capacitors without departing from the scope of this disclosure. Accordingly, the electrode 100 will be described herein as being configured for use with a capacitor such as an electrolytic capacitor without being restricted to the particular capacitor types shown and described herein.

The electrode 100 is provided as a multilayer structure 104 and includes a substrate or base material 110, a carbide layer 120, and a layer of material 130 (i.e., a carbonaceous or carbon-containing layer) that acts to enhance the capacitance of the electrode 100. In this manner, the carbonaceous layer 130 may be referred to as a capacitance-enhancing material or layer. An electrolyte 140 is in contact with the carbonaceous layer 130.

The substrate 110 is a metal selected from titanium, aluminum (for an anode), tantalum, niobium, zirconium, silver, stainless steel, and alloys of any one or more of the foregoing metals. The particular substrate material chosen may depend on a variety of factors. Where the substrate is part of a cathode, the substrate material is preferably relatively tough, weldable, and resistant to chemicals. For example, a substrate for a cathode may be titanium or a titanium alloy. In other examples, the cathode may include a substrate made of tantalum, niobium, or alloys thereof. Other materials may also be used.

Where the substrate is part of an anode, the material chosen preferably has the capability to form an anodic oxide thereon. Because such metals allow electrons generally to travel in one direction but not another (i.e., due to the interface between the metal and an oxide formed thereon), such materials may generally be referred to as valve metals. For example, a substrate for use in an anode may be aluminum, tantalum, niobium, or alloys thereof. Other materials may also be used.

While any of a variety of materials may be used for the substrate, according to a preferred embodiment, the substrate 110 is titanium or a titanium alloy (e.g., titanium or titanium alloy foil or sheet metal). According to an alternative embodiment (in an anode), the substrate is aluminum or an aluminum alloy. According to various other alternative embodiments, the substrate may comprise a glassy carbon material or any other material that may be acceptable for use as an electrode substrate.

The substrate 110 may be provided as a single layer of material or may include multiple layers of material. The various layers may have the same composition or may differ from each other (e.g., a substrate may be provided as having alternating layers of titanium and a titanium alloy). It should be noted that the materials described for the substrate 110 are not exclusive, and other metals or materials may be utilized according to alternative embodiments.

According to a preferred embodiment, the substrate 110 has a thickness of between approximately 150 and 250 micrometers. According to various alternative embodiments, the substrate may have a thickness of between approximately 50 and 500 micrometers.

According to a preferred embodiment, the substrate 110 includes a surface 112 that has a relatively rough characteristic or configuration (e.g., the surface 112 is not entirely planar or flat, and may include protrusions or extensions that extend from the surface 112 to form a surface having peaks and valleys). One nonexclusive example of such a surface is shown in FIG. 6, although the precise nature of such a surface may vary according to alternative embodiments. According to a preferred embodiment, the surface 112 has a roughness of between approximately 2 and 5 micrometers (e.g., the average height or distance between the peaks and valleys is between 2 and 5 micrometers). It is intended that the roughness of the surface 112 provides for enhanced mechanical bonding between the substrate 110 and a layer of material provided in contact with the substrate 110. Chemical bonding may be utilized in addition to mechanical bonding to secure such a layer of material to the substrate 110.

While it is preferred that the surface 112 has a relatively rough surface finish to provide for enhanced mechanical bonding, according to an alternative embodiment, the surface of the substrate may have a relatively flat or planar surface finish. In such a case, chemical bonding may play a larger role in bonding a layer of material to the substrate.

According to an exemplary embodiment, the substrate has a relatively thin (e.g., less than approximately 10 nanometers) native oxide layer. For example, according to a preferred embodiment in which the substrate 110 is titanium or a titanium alloy, the substrate 110 may include a relatively thin titanium oxide layer on the surface 112 thereof.

The carbide layer 120 is provided adjacent or proximate (e.g., in contact with) the substrate 110. According to an exemplary embodiment, the carbide layer 120 is a metal carbide comprising carbon atoms and metal atoms as provided in the adjacent substrate 110. For example, according to a preferred embodiment in which the substrate 110 is titanium, the carbide layer 120 is titanium carbide (TiC). Other types of carbides may also be utilized. In providing the carbide layer 120, oxygen atoms included in the native titanium oxide layer may be displaced by carbon atoms in an elevated temperature reaction as will be described in greater detail below. According to an alternative embodiment, no carbide layer is provided (e.g., where the substrate comprises aluminum or an aluminum alloy, as in an anode application). According to still other alternative embodiments, an additional layer of material may be provided intermediate or between the substrate and the carbide layer.

The carbide layer 120 is bonded or coupled both chemically (e.g., is a chemisorbed layer) and mechanically (e.g., by virtue of interaction between the carbide and the roughened surface 112 of the substrate 110) to the substrate 110 according to a preferred embodiment. According to an alternative embodiment, the carbide layer may be coupled by purely mechanical or purely chemical means to the surface.

The carbide layer 120 is formed by providing a layer of carbon-containing material (e.g., graphite powder or particles with individual particle sizes of about 1 micrometer) adjacent the substrate 110. According to a preferred embodiment, the layer of carbon has a thickness of between approximately 20 and 30 micrometers and is deposited as up to 10 or more coats or layers of a graphite powder suspension in a carrier liquid. According to alternative embodiments, the layer of carbon may be provided as having a different thickness and/or may be applied in a different number of coats or layers.

An elevated temperature or vacuum baking step is performed in which the carbon-containing material is subjected to a temperature of between approximately 8000 and 1000° C. in a vacuum furnace at a pressure of approximately 10E-6 Torr, during which at least a portion of the carbon included in the carbon-containing material forms a metal carbide (e.g., by displacing oxygen atoms in the native oxide formed on the surface of the substrate). According to a preferred embodiment, at least a portion of the carbon-containing material is not converted to a carbide material, and remains as bulk carbon-containing material adjacent the carbide layer 120. According to an alternative embodiment, the carbon-containing material is entirely consumed in the vacuum baking step, such that no carbon-containing material is left adjacent the carbide layer. In yet another alternative embodiment, the vacuum baking step may be replaced with an elevated temperature process performed in an inert (e.g., argon) atmosphere.

According to a preferred embodiment, the thickness of the carbide layer 120 is less than approximately 10 nanometers. According to alternative embodiments, the thickness of the carbide layer may be greater than 10 nanometers (e.g., between approximately 10 and 500 nanometers).

The carbonaceous layer 130 is provided adjacent or proximate the carbide layer 120, and provides enhanced capacitance for the electrode 100. The carbonaceous layer 130 includes activated carbon (formed from the carbon-containing material provided adjacent the carbide layer 120) and an oxide of manganese (e.g., manganese dioxide ($MnO_2$)). The carbonaceous layer may also include unreacted (e.g., non-activated) carbon-containing material intermediate or between the activated carbon and the carbide layer. According to an alternative embodiment, the carbon provided in the carbonaceous layer is not activated, and instead includes carbon (e.g., graphite) and an oxide of manganese.

As described above, according to a preferred embodiment, a portion of the carbon-containing material remains adjacent the carbide layer after the vacuum baking step that converts a portion of the carbon-containing layer to a metal carbide material. According to an alternative embodiment, additional carbon-containing material (either the same as or different from the carbon-containing material used to form the carbide layer) may be provided adjacent the carbide layer.

The substrate 110 and the carbide layer 120 (and any remaining or deposited carbon-containing material) may be cooled to a temperature of between approximately 20° and 100° C. and then heated in an oxygen-containing atmosphere or ambient (e.g., air, pure oxygen, etc.) to a temperature of between approximately 400° and 450° C. for a period of between approximately 30 and 90 minutes. This heating step serves to activate at least a portion of the carbon-containing material provided adjacent the carbide layer 120 by forming functional groups that include oxygen. For example, an activated carbon region 134 formed in the carbonaceous layer 130 may include oxygen-containing functional groups such as CO, COOH, and C=O.

The activated carbon region 134 exhibits increased porosity as compared to the carbon-containing material from which it is formed, which allows liquid electrolyte to penetrate at least a portion of the carbonaceous layer 130. One advantageous feature of providing an activated carbon region 134 is that the surface area of the carbonaceous layer 130 is increased, which in turn acts to increase the capacitance of the electrode 100.

The thickness of the activated carbon region 134 is a function of the amount of time that elapses during the elevated temperature activation. According to a preferred embodiment, the thickness of the carbonaceous layer 130 is between approximately 10 and 50 micrometers, and the thickness of the activated carbon region 134 is between approximately 5 and 25 micrometers after activating the carbon-containing material at a temperature of approximately 250° C. for a period of approximately 0.5 hours. A layer 136 of unreacted (e.g., non-activated) carbon-containing material remains intermediate or between the activated carbon region 134 and the carbide layer 120. According to another embodiment, the activated carbon portion of the carbonaceous layer extends entirely through the carbonaceous layer so that substantially all of the carbon-containing material is provided as activated carbon.

The carbonaceous layer 130 also includes an oxide of manganese (e.g., manganese dioxide ($MnO_2$)). According to a preferred embodiment, manganese nitrate ($Mn(NO_3)_2$) is provided in solution with water and an alcohol, after which the manganese nitrate is heated to provide an oxide of manganese. The solution of manganese nitrate, water, and alcohol penetrates the relatively porous activated carbon region 134, and upon heating the activated carbon region 134 and the solution, a fine dispersion of oxide is provided in the pores of the activated carbon region 134. It is intended that the inclusion of metal oxide in the carbonaceous layer 130 acts to further enhance the capacitance of the electrode 100.

Figure 10:
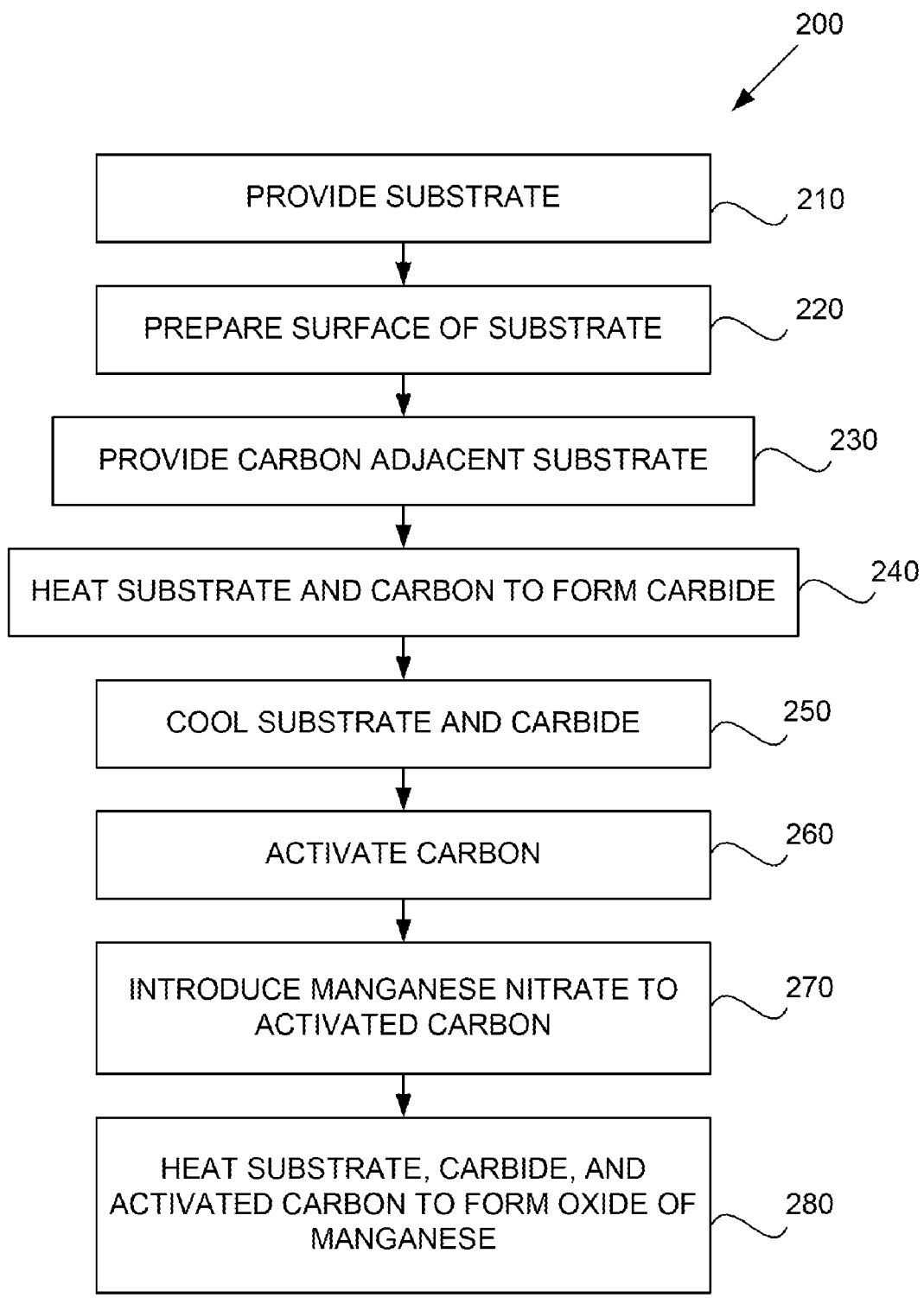
FIG. 10 is a flow diagram illustrating a process for forming the portion of the capacitor shown in FIG. 6.

A method or process 200 of preparing the electrode 100 is now described with reference to FIGS. 6-9. A flow diagram illustrating such a method or process 200 is provided as FIG. 10.

As shown in FIG. 6, the substrate 110 is provided in a step 210. According to a preferred embodiment, the substrate 110 is titanium or a titanium alloy and is provided as a foil or sheet of metal. According to alternative embodiments, the substrate may be made of aluminum or a variety of other materials acceptable for use in capacitor electrodes as described above.

In a step 220, a surface 112 of the substrate 110 is altered or deformed to have a relatively rough characteristic or configuration. Various methods may be used to provide the surface 112 with its relatively rough surface finish. For example, according to an exemplary embodiment, a grit blasting technique may be utilized to alter the surface 112. The grit may be alumina ($Al_2O_3$) or silicon carbide (SiC) having a particle diameter of about 1 micrometer. The grit may be accelerated using compressed air at pressures between approximately 20 and 40 psi.

According to another exemplary embodiment, an etching process may be utilized to provide the surface 112 with a relative surface finish. For example, oxalic acid may be utilized at a temperature of approximately 80° C.

According to another exemplary embodiment, the substrate may be provided with a roughened surface without the need to perform a separate processing step. For example, sintered metal particles (e.g., sintered titanium) may be deposited on a metal sheet surface (e.g., a titanium sheet) using a vacuum sintering process.

In a step 230, a carbon layer 115 (e.g., a layer of carbon-containing material) is provided adjacent at least a portion of the substrate 110. According to a preferred embodiment, the carbon layer 115 may be provided as a suspension of carbon or graphite powder in alcohol (e.g., methanol, isopropanol, etc.), and may be provided in either a polymerizable or non-polymerizable form.

The carbon layer 115 may be deposited or formed by any suitable means. According to a preferred embodiment, the carbon layer 115 may be provided using a spray gun or an equivalent alternative device. Other methods for providing the carbon layer 115 may also be used according to alternative embodiments (e.g., sputtering, chemical vapor deposition, physical vapor deposition, etc.). The particular deposition method may be chosen based on a variety of factors, including cost, manufacturability, and desired characteristics for the deposited material.

According to a preferred embodiment, the carbon layer 115 includes graphite particles having particle sizes of approximately 1 micrometer (e.g., between approximately 0.1 and 2 micrometers). One nonexclusive example of such material is commercially available as a graphite, colloidal, lubricant, aerosol spray by Alfa Aesar of Ward Mill, Mass. The carbon material is provided as a suspension of graphite in isopropanol. According to alternative embodiments, other types of alcohol may be used in place of or in addition to isopropanol.

According to an exemplary embodiment, the carbon layer 115 includes multiple layers of carbon-containing material that are deposited in multiple deposition steps. For example, the carbon layer 115 may include between 3 and 20 layers of carbon-containing material and may have a thickness of between approximately 20 and 30 micrometers. The number of layers and the thickness of the carbon layer may vary according to a variety of alternative embodiments.

Figure 8:
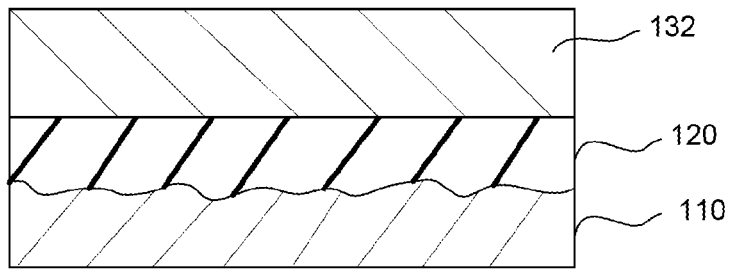
FIG. 8 is a schematic cross-sectional view of the portion of the capacitor shown in FIG. 6 showing a carbide formation step.
Figure 9:
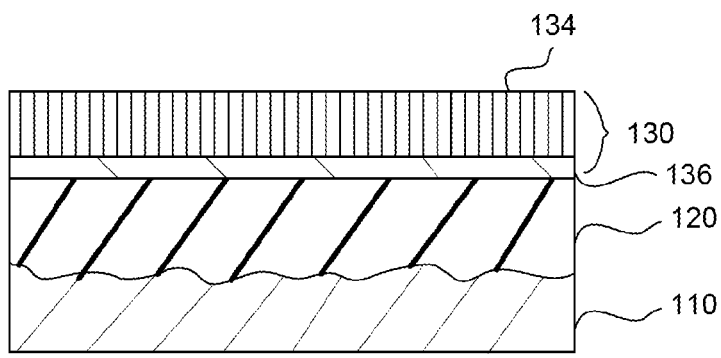
FIG. 9 is a schematic cross-sectional view of the portion of the capacitor shown in FIG. 6 showing the formation of a capacitance-enhancing layer.

As shown in FIG. 8, in a step 240 (FIG. 10), the substrate 110 and the carbon layer 115 are heated to a temperature of between approximately 800° and 1000° C. at a pressure of approximately 10E-6 Torr for approximately 1 hour (e.g., between approximately 30 and 90 minutes). During this vacuum baking step, alcohol provided with the carbon-containing material is evaporated and/or pyrolized. At least a portion of the carbon atoms included in the layer of carbon material 115 chemically react with metal atoms to form a carbide layer 120. For example, according to a preferred embodiment in which the substrate is made of titanium, a titanium carbide layer is formed during the vacuum baking step. The carbon atoms may displace oxygen atoms in the native oxide (e.g., titanium dioxide) formed on the surface of the substrate and/or may react with metal atoms included in the substrate. Where the substrate is provide as aluminum or an aluminum alloy, the vacuum baking step may be omitted.

The thickness of the carbide layer 120 may at least in part be determined by the amount of time the substrate 110 and carbon layer 115 are heated in the vacuum baking step. According to an exemplary embodiment, only a portion of the carbon layer 115 is consumed during the vacuum baking step, and a layer of unreacted carbon-containing material 132 remains adjacent the carbide layer 120. According to an alternative embodiment, the entire carbon layer 115 is consumed in the vacuum baking step and another layer of carbon-containing material may be provided adjacent the carbide layer. The additional layer of carbon-containing material may have a composition which is the same as or different from that of the carbon material used to form the carbide layer.

In a step 250, the substrate 110, the carbide layer 120, and the unreacted carbon layer 132 is cooled to a temperature of between approximately 20° and 100° C.

The substrate 110, the carbide layer 120, and the unreacted carbon layer 132 are heated in a step 260 (FIG. 9) to a temperature of between approximately 300° and 500° C. in an oxygen-containing ambient or atmosphere (e.g., air, pure oxygen, etc.) for a period of between approximately 30 and 90 minutes. In this step, at least a portion of the unreacted carbon layer 132 is activated such that oxygen-containing functional groups such as CO, COOH, and C=O are created to form an activated carbon region 134.

The carbonaceous layer 130 includes an activated carbon region 134 and an unreacted or non-activated carbon region 136 (which has a thickness less than the unreacted carbon layer 132 according to an exemplary embodiment. The unreacted carbon region 136 includes non-activated carbon-containing material. According to an alternative embodiment, the entire unreacted carbon layer 132 is converted to activated carbon such that there is no unreacted carbon left in the carbonaceous layer 130.

The relative thicknesses of the activated carbon region 134 and the unreacted carbon region 136 are a function of the amount of time that elapses during the activation step. According to an exemplary embodiment, the thickness of the activated layer is between approximately 40 and 50 micrometers after heating at approximately 450° C. for approximately 30 minutes.

In a step 270, a solution of manganese nitrate ($Mn(NO_3)_2$) is introduced to the activated carbon region 134 of the carbonaceous layer 130. Because the activated carbon region 134 is relatively porous, the solution penetrates into at least a portion of the carbonaceous layer 130 (i.e., the solution infiltrates at least a portion of the carbonaceous layer 130).

The manganese nitrate solution includes manganese nitrate and an alcohol such as ethanol, methanol, or isopropanol. Water is included in the solution. According to a preferred embodiment, the solution comprises between approximately 5 and 50 weight percent manganese nitrate, between approximately 25 and 75 volume percent water, and between approximately 25 and 75 volume percent methanol. According to alternative embodiments, the proportions of the various constituents of the solution may be varied (e.g., water may be eliminated from the solution).

In a step 280, the substrate 110, the carbide layer 120, and the carbonaceous layer 130 (including the manganese nitrate solution) are heated to a temperature of between approximately 150° and 350° C. in an oxygen-containing atmosphere for a period of between approximately 3 and 90 minutes. According to other exemplary embodiments, a temperature of up to approximately 400° C. may be used. Prior to this step, a pre-treatment step (e.g., pre-drying or related treatments as are known to those of skill in the art) may be performed. The environment in the pyrolysis chamber in which such steps are performed may include water steam or related agents as are well known. According to a preferred embodiment, the manganese nitrate solution is heated to a temperature of approximately 250° C. for approximately 60 minutes. As a result of this heating step, all or nearly all of the manganese nitrate is converted to an oxide of manganese (e.g., manganese dioxide). The oxide is provided as finely dispersed particles embedded in the activated carbon region 134.

The oxide acts to further enhance the capacitance of the electrode 100. According to an exemplary embodiment, the capacitance of the electrode 100 is greater than approximately 10 milliFarads per square centimeter. According to another exemplary embodiment, the capacitance of the electrode 100 is greater than approximately 20 milliFarads per square centimeter.

Figure 11:
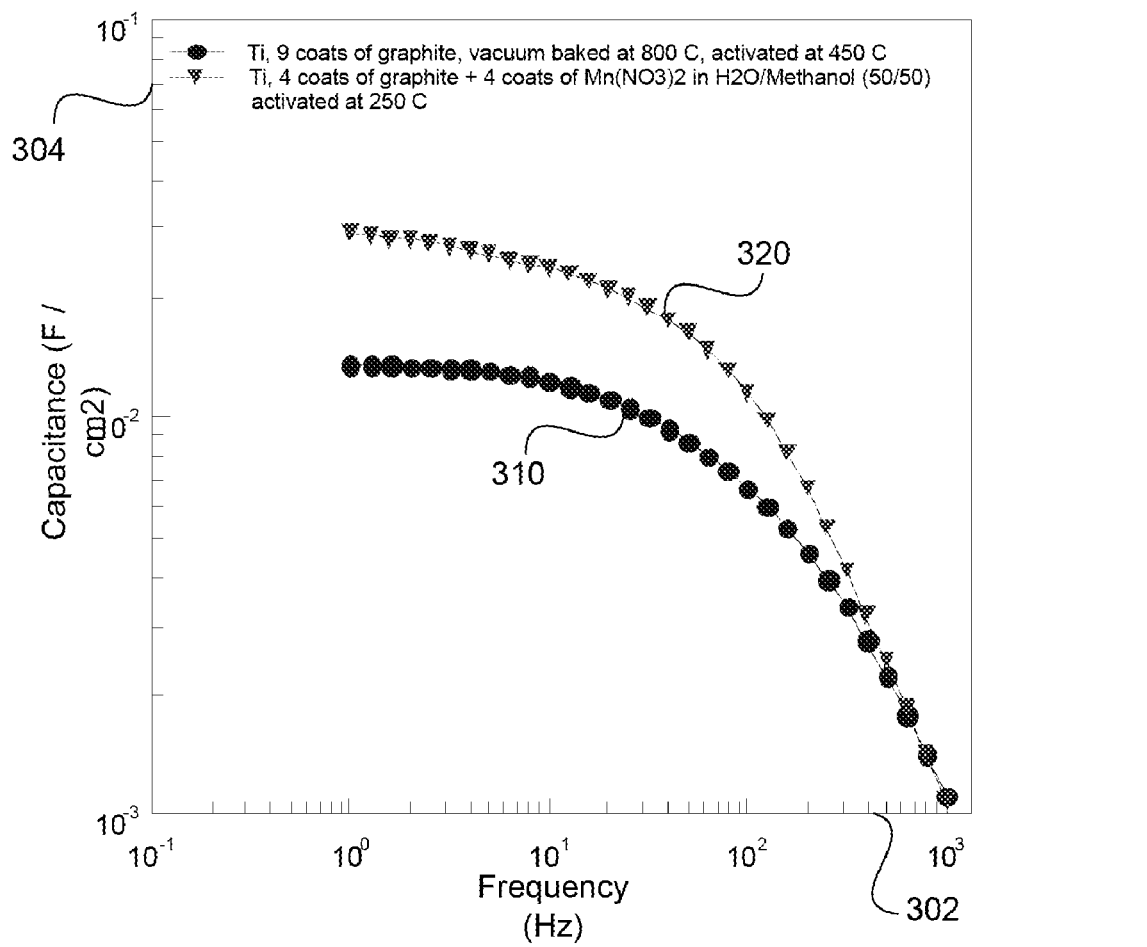
FIG. 11 is a graphical representation showing the capacitance verses frequency functionality for electrodes having a titanium substrate.

FIG. 11 shows a graph 300 illustrating capacitance over frequency functionality for electrodes having a carbonaceous electrode coatings provided over a titanium substrate. Both the abscissa 302 and the ordinate 304 are provided as logarithmic scales. A first curve 310 illustrates capacitance versus frequency functionality for an electrode having nine coats of carbon provided over a titanium substrate using a suspension including graphite in isopropanol vacuum baked at 800° C. and activated at a temperature of 450° C. for one hour. A second curve 320 illustrates capacitance versus frequency functionality for an electrode having four coats of graphite and enriched with manganese dioxide. The manganese dioxide is provided by introducing four coats of manganese nitrate dissolved in methanol and water (50 percent water, 50 percent methanol) and heating to 250° C. for 45 minutes in air. As shown in the graph 300, the capacitance of the electrodes enriched with manganese dioxide is greater than that of the electrode including only activated carbon.

One advantageous feature of providing manganese nitrate in solution with an alcohol to form a capacitance-enhancing carbonaceous layer enriched with an oxide of manganese is that degradation or damage to the underlying carbide layer and/or substrate is reduced or eliminated during processing. Such advantage may also be obtained when utilizing other nitrates or metal oxide precursors.

Figure 12:
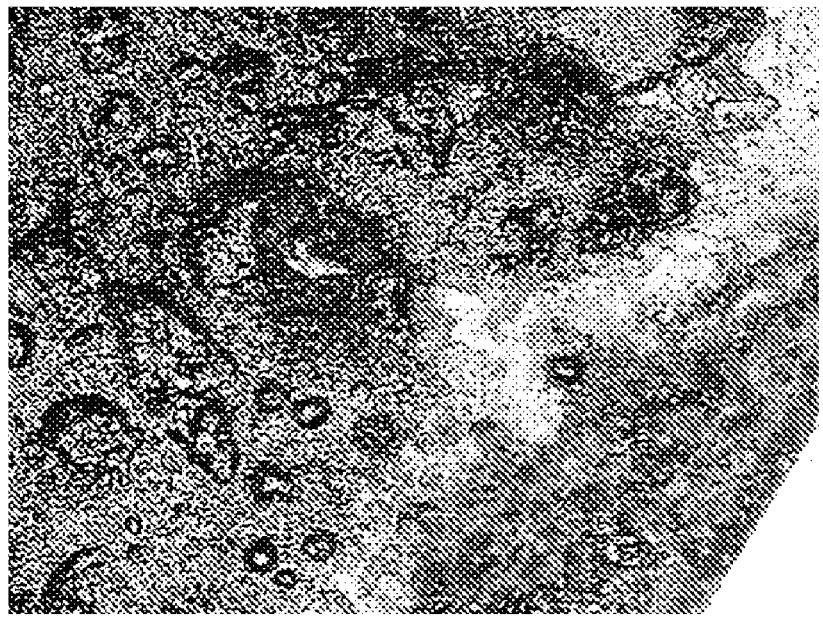
FIG. 12 is a micrograph showing an electrode surface having a damaged or ruptured characteristic.

FIG. 12 shows a micrograph (magnified to 10×) of a manganese-dioxide enriched carbonaceous layer provided over a titanium substrate and a titanium carbide layer. The carbonaceous layer was prepared by utilizing a manganese nitrate and water solution. As shown, use of such a solution produced a ruptured or damaged carbonaceous layer. It is believed that the damage to the carbonaceous layer was a result of an elevated-temperature reaction between the manganese nitrate and the titanium substrate underlying the titanium carbide layer during the formation of manganese dioxide. The result is a ruptured and damaged carbonaceous layer.

Figure 13:
FIG. 13 is a micrograph showing an electrode surface having a relatively smooth characteristic.

FIG. 13 shows a micrograph (magnified to 10×) of a manganese dioxide enriched carbonaceous layer prepared by utilizing a manganese nitrate, water, and methanol solution. Providing alcohol in solution with the manganese nitrate produced a relatively smooth, high-capacitance carbonaceous layer that does not exhibit the same defects found when a manganese nitrate and water solution were utilized (FIG. 12). In this manner, the alcohol provided in solution with the manganese nitrate acts as a reducing agent which reduces or eliminates the reaction between the manganese nitrate and the underlying metal substrate layer. As a result, a relatively smooth and defect-free carbonaceous layer may be produced.

As utilized herein, the terms "approximately," "about," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The construction and arrangement of the elements of the capacitor as shown in the preferred and other exemplary embodiments is illustrative only. Although only a few embodiments of the present inventions have been described in detail in this disclosure, those skilled in the art who review this disclosure will readily appreciate that many modifications are possible without materially departing from the novel teachings and advantages of the subject matter recited in the claims. Accordingly, all such modifications are intended to be included within the scope of the present invention as defined in the appended claims. The order or sequence of any process or method steps may be varied or re-sequenced according to alternative embodiments. Materials or layers that are "adjacent" or "proximate" each other may be in contact with each other or may be separated by another material or layer, or by a plurality of such materials or layers. Other substitutions, modifications, changes and omissions may be made in the design, operating conditions and arrangement of the preferred and other exemplary embodiments without departing from the scope of the present invention as expressed in the appended claims.

What is claimed is:

1. A method of making an electrolytic capacitor comprising:
    providing a first electrode comprising a metal substrate, a carbide layer, and a carbonaceous material that includes activated carbon, the metal substrate comprising a metal selected from the group consisting of titanium, aluminum, tantalum, niobium, zirconium, silver, steel, and alloys and combinations thereof;
    providing a second electrode; and
    providing an electrolyte.

2. The method of claim 1, further comprising roughening a surface of the substrate.

3. The method of claim 2, wherein the roughening step utilizes at least one process selected from the group consisting of grit blasting and etching.

4. The method of claim 2, wherein the roughness of the surface as measured by the distance between peaks and valleys at the surface is between approximately 2 and 5 micrometers.

5. The method of claim 1, further comprising providing a material comprising carbon adjacent the substrate and subjecting the material comprising carbon to a temperature of between approximately 800 and 1000 degrees Celsius to form the carbide layer.

6. The method of claim 5, wherein the step of providing a material comprising carbon adjacent the substrate comprises depositing the material comprising carbon on the substrate.

7. The method of claim 5, wherein the material comprising carbon comprises graphite.

8. The method of claim 1, wherein the step of providing a first electrode comprises providing the carbonaceous material adjacent the carbide layer and heating the carbonaceous material in an oxygen-containing atmosphere to activate at least a portion of the carbonaceous material to form the activated carbon.

9. The method of claim 8, further comprising introducing an oxide of manganese into the carbonaceous material.

10. The method of claim 9, wherein the step of introducing an oxide of manganese into the carbonaceous material comprises providing a solution comprising manganese nitrate and heating the solution and the carbonaceous material to form the oxide of manganese.

11. The method of claim 8, wherein the step of heating the carbonaceous material in an oxygen-containing atmosphere to activate at least a portion of the carbonaceous material comprises heating the carbonaceous material to a temperature of between approximately 300 and 500 degrees Celsius for a period of between approximately 30 and 90 minutes.

12. The method of claim 8, wherein the step of heating the carbonaceous material in an oxygen-containing atmosphere produces a carbonaceous layer having a layer of the activated carbon and a layer of non-activated carbon.

13. The method of claim 1, wherein the substrate comprises titanium.

14. The method of claim 1, wherein the substrate comprises aluminum.

15. The method of claim 1, further comprising forming a native oxide layer on the substrate.

16. The method of claim 1, wherein the carbide layer comprises a metal carbide.

17. A method of making an electrolytic capacitor comprising:
    preparing a first electrode by providing a carbide layer and a carbonaceous layer on a metal substrate, the carbonaceous layer comprising activated carbon and the metal substrate comprising a metal selected from the group consisting of titanium, aluminum, tantalum, niobium, zirconium, silver, and steel, and alloys and combinations thereof; and
    providing the first electrode in a housing along with a second electrode and an electrolyte.

18. The method of claim 17, further comprising roughening a surface of the substrate such that the roughness of the surface as measured by the distance between peaks and valleys at the surface is between approximately 2 and 5 micrometers.

19. The method of claim 17, further comprising providing a carbon-containing material adjacent the substrate and subjecting the carbon-containing material to a temperature of between approximately 800 and 1000 degrees Celsius to form the carbide layer.

20. The method of claim 17, wherein the carbonaceous layer includes both activated and non-activated carbon.

21. The method of claim 17, further comprising introducing an oxide of manganese into the carbonaceous layer.

22. The method of claim 21, wherein the step of introducing an oxide of manganese into the carbonaceous layer comprises providing a solution comprising manganese nitrate and heating the solution and the carbonaceous layer to form the oxide of manganese.

23. The method of claim 17, wherein the substrate comprises a metal selected from the group consisting of titanium and aluminum.

24. The method of claim 17, wherein the carbide layer comprises a metal carbide.

25. A method of making an electrolytic capacitor comprising:
    providing a first layer of material and a second layer of material on a substrate to form a first electrode, the first layer of material comprising a carbide and the second layer of material comprising a carbonaceous material, the substrate formed from a metal selected from the group consisting of titanium, aluminum, tantalum, niobium, zirconium, silver, and steel, and alloys and combinations thereof;
    providing the first electrode in a housing;
    providing a second electrode in the housing; and
    providing an electrolyte in the housing.

26. The method of claim 25, further comprising roughening a surface of the substrate using a process selected from the group consisting of grit blasting and etching.

27. The method of claim 26, wherein the roughness of the surface is between approximately 2 and 5 micrometers.

28. The method of claim 25, further comprising providing graphite adjacent the substrate and subjecting the graphite to a temperature of between approximately 800 and 1000 degrees Celsius to form the first layer.

29. The method of claim 28, wherein the graphite is provided as a suspension of graphite powder in alcohol.

30. The method of claim 25, wherein the step of providing the second layer of material comprises heating the carbonaceous material in an oxygen-containing atmosphere to activate at least a portion of the carbonaceous material.

31. The method of claim 30, further comprising introducing an oxide of manganese into the carbonaceous material.

32. The method of claim 31, wherein the step of introducing an oxide of manganese into the carbonaceous material comprises providing a solution comprising manganese nitrate and heating the solution and the carbonaceous material to form the oxide of manganese.

33. The method of claim 25, wherein the substrate comprises titanium or aluminum.

34. The method of claim 25, wherein the carbide comprises a metal carbide.

* * * * *